United States Patent
Li et al.

(10) Patent No.: US 11,506,650 B2
(45) Date of Patent: Nov. 22, 2022

(54) METHOD FOR AUTOMATIC QUANTITATIVE STATISTICAL DISTRIBUTION CHARACTERIZATION OF DENDRITE STRUCTURES IN A FULL VIEW FIELD OF METAL MATERIALS

(71) Applicant: The NCS Testing Technology Co., Ltd., Beijing (CN)

(72) Inventors: Dongling Li, Beijing (CN); Weihao Wan, Beijing (CN); Jie Li, Beijing (CN); Haizhou Wang, Beijing (CN); Lei Zhao, Beijing (CN); Xuejing Shen, Beijing (CN); Yunhai Jia, Beijing (CN)

(73) Assignee: THE NCS TESTING TECHNOLOGY CO., LTD., Beijing (CN)

( * ) Notice: Subject to any disclaimer, the term of this patent is extended or adjusted under 35 U.S.C. 154(b) by 324 days.

(21) Appl. No.: 17/009,117

(22) Filed: Sep. 1, 2020

(65) Prior Publication Data

US 2021/0063376 A1 Mar. 4, 2021

(30) Foreign Application Priority Data

Sep. 3, 2019 (CN) .......................... 201910826312.0

(51) Int. Cl.
*G06T 7/00* (2017.01)
*G01N 33/204* (2019.01)
(Continued)

(52) U.S. Cl.
CPC ............ *G01N 33/204* (2019.01); *G01N 1/32* (2013.01); *G01N 1/4044* (2013.01); *G06T 7/11* (2017.01);
(Continued)

(58) Field of Classification Search
CPC ...... G01N 33/204; G01N 1/32; G01N 1/4044; G01N 21/84; G01N 2021/8477;
(Continued)

(56) References Cited

U.S. PATENT DOCUMENTS

2019/0053790 A1* 2/2019 Grover .................. A61L 31/047
2019/0278880 A1* 9/2019 Ma .......................... G06F 30/20
(Continued)

FOREIGN PATENT DOCUMENTS

CN 108226159 A 6/2018

OTHER PUBLICATIONS

Zhang et al., "Primary Dendrite Spacing in Single Crystal Superalloy Prepared by Directional Solidification," Foundry Technology, Jan. 2018, vol. 39 No. 01, pp. 21-24, 4 pages.
(Continued)

*Primary Examiner* — Ping Y Hsieh
(74) *Attorney, Agent, or Firm* — Muncy, Geissler, Olds & Lowe, P C.

(57) ABSTRACT

The invention belongs to the technical field of quantitative statistical distribution analysis for micro-structures of metal materials, and relates to a method for automatic quantitative statistical distribution characterization of dendrite structures in a full view field of metal materials. According to the method based on deep learning in the present invention, dendrite structure feature maps are marked and trained to obtain a corresponding object detection model, so as to carry out automatic identification and marking of dendrite structure centers in a full view field; and in combination with an image processing method, feature parameters in the full view field such as morphology, position, number and spacing of all dendrite structures within a large range are obtained quickly, thereby achieving quantitative statistical distribution characterization of dendrite structures in the
(Continued)

metal material. The method is accurate, automatic and efficient, involves a large amount of quantitative statistical distribution information, and is statistically more representative as compared with the traditional measurement of feature sizes of dendrite structures in a single view field.

12 Claims, 11 Drawing Sheets

(51) Int. Cl.
  *G06T 7/62* (2017.01)
  *G06T 7/11* (2017.01)
  *G01N 1/32* (2006.01)
  *G01N 1/40* (2006.01)
(52) U.S. Cl.
  CPC ...... *G06T 7/62* (2017.01); *G06T 2207/20081* (2013.01); *G06T 2207/30136* (2013.01)

(58) Field of Classification Search
  CPC ... G06T 7/11; G06T 7/62; G06T 2207/20081; G06T 2207/30136; G06N 3/08
  See application file for complete search history.

(56) References Cited

U.S. PATENT DOCUMENTS

2020/0003682 A1* 1/2020 Frenkel .................. G06N 20/00
2021/0056678 A1* 2/2021 Al Shehri ............. G06N 3/084

OTHER PUBLICATIONS

Chowdhury et al., "Image driven machine learning methods for microstructure recognition," Computational Materials Science, 2016, vol. 123, pp. 176-187, 12 pages.

* cited by examiner

METHOD FOR AUTOMATIC QUANTITATIVE STATISTICAL DISTRIBUTION CHARACTERIZATION OF DENDRITE STRUCTURES IN A FULL VIEW FIELD OF METAL MATERIALS

FIELD OF THE INVENTION

The invention belongs to the technical field of quantitative statistical distribution analysis on feature maps of microstructures of metal materials, and relates to a method for automatic quantitative statistical distribution characterization of dendrite structures in a full view field of metal materials.

BACKGROUND OF THE INVENTION

A dendrite structure is a feature structure produced during directional solidification of a metal material. It is caused by element segregation at a solid-liquid interface during the non-equilibrium solidification of an alloy and is closely related to a solidification process. A feature parameter for characterizing the dendrite structure is a dendrite spacing, and has a decisive influence on the properties of the material. Especially for a nickel-based single crystal superalloy, which a preferred material for a turbine blade of an aero engine, a cross dendrite structure is a main structure thereof, and its feature parameter directly influences the thermomechanical properties and heat treatment process of the alloy.

According to an early solidification theory, a corresponding solidification structure under certain solidification conditions and its size are unique. However, recent experimental research shows that under certain solidification conditions, a dendrite and cell spacing has an allowable range, within which the specific spacing is related to the solidification history [Hunt J D, Lu S Z. Numerical modeling of cellular/dendrite array growth: spacing structure prediction [J]. Metallurgical and Materials Transactions, 1996, 173(3): 611-623.]. Therefore, it is necessary to carry out further research on the distribution of dendrite spacings, so as to investigate the stability and reliability of the solidification process. A primary dendrite spacing refers to the distance between dendrite cores of two neighboring dendrites. A direct measurement method is widely used to determine a primary dendrite pacing. However, this method has low statistical efficiency and is only suitable for measuring a small number of dendrite spacings. The national standard of China GB/T14999.7-2010 specifies a method for measuring primary dendrite spacings in superalloy casts: calculating the number of primary dendrites in a single field of view, and determining the area of a picture by conversion according to a metallographic magnification, and finally, calculating an average spacing between the primary dendrites in the field of view according to a formula. This method requires manual identification of the number of primary dendrites in the field of view. It also has the problem of low efficiency and cannot reflect primary dendrite spacings in different locations and regions, nor achieve statistical quantitative distribution of all primary dendrite spacings on a large-size cross-section of the material. Therefore, the measurement of the average spacing between primary dendrites in a single field of view still cannot meet the needs of material workers to investigate the solidification process and improve the material performance.

At present, the difficulties that hinder the rapid detection of dendrite structure feature parameters in metal materials mainly include the irregular shape of dendrites, and the uniformity of the background gray level of each picture cannot be guaranteed during image acquisition, which leads to a large error of results for parallel image processing. Therefore, the conventional identification and counting of primary dendrites is usually carried out manually [Zhang Xiaoli, Zhang Yanan, Liu Guiquna, et al., Study on Primary dendrite Spacings of Single Crystal Superalloys Prepared by Directional Solidification [J]. Foundry Technology, 2018.39 (1):21-24], and statistical results cannot be provided through quantitative metallographic software as in the case of a regular spheroidal particle structure. A macro metal material is essentially a collection of heterogeneous micro-structures. The observation of structures in a single field of view or locally multiple fields of view cannot reflect overall distribution features of the micro-structures of the material, and primary dendrites at the edges of a single field of view cannot be involved in statistics due to incomplete observation, which led to a further reduced number of complete dendrites that can be involved in the statistics. If multiple fields of view were randomly acquired for manual identification and direct spacing measurement of primary dendrites, the number of dendrites involved in statistics is increased, but the sample regions represented by the random fields of view are split, which still leads to the problem of insufficient statistical representation.

SUMMARY OF THE INVENTION

In view of the above technical problems, and taking into account the existing non-uniformity of microstructures of materials, an object of the present invention is to provide a method for full-field automatic identification, positioning, measurement and statistical characterization of dendrite structures in a full view field of metal materials based on deep learning, so as to eliminate subjective errors caused by manual selection of a field of view and solves the problem of low efficiency due to manual identification, measurement and statistics of dendrite structures, thereby quickly obtaining information, such as morphology, position, quantity, spacing, of all dendrite structures of metal materials within a large range, and achieving quantitative statistical distribution characterization of all dendrite structures in the full view field, and providing a more representative means for comprehensive, accurate, automatic and efficient detection of dendrite structures in metal materials.

To achieve the above object, the present invention provides the following technical solution:

A method for automatic quantitative statistical distribution characterization of dendrite structures in a full field of view of metal materials includes the following steps:

(1) Establishment of an Object Detection Model Based on Deep Learning performing metallographic sample preparation, polishing and chemical corrosion on a standard metal material sample with the same material as a metal material to be detected, so that the surface of the sample shows a clear and complete dendrite structure;

acquiring dendrite structure feature maps of the standard metal material sample after the metallographic chemical corrosion by using a fully automatic metallographic microscope, and establishing a dendrite structure feature map data set; labeling images in the dendrite structure feature map data set by using dendrite centers as objects to obtain images containing marker boxes, with the dendrite centers being inside the marker boxes, wherein labeled information includes a category and regional information of the object, the category indicating whether the marker box contains the dendrite center, and the regional information including the position of the dendrite center; and generating an object detection sample library from the marked dendrite structure feature map data set; and establishing an object detection network, and training with the obtained object detection sample library to obtain an object detection model;

(2) Automatic Acquisition of Dendrite Structure Feature Maps in a Full View Field of the Metal Material to be Detected performing metallographic sample preparation and metallographic chemical corrosion on the metal material to be detected, by using the same metallographic sample preparation and metallographic chemical corrosion process as in step (1), and then automatically acquiring dendrite structure feature maps in a full view field of the surface of the metal material to be detected after the metallographic chemical corrosion, by using a fully automatic metallographic microscope;

(3) Automatic Identification and Rapid Positioning of Dendrite Structures inputting all images to be detected acquired in step (2) into the object detection model established in step (1), to directly obtain dendrite structure feature maps marked with the dendrite centers;

(4) Automatic Stitching and Fusion of the Dendrite Structure Feature Maps in a Full View Field identifying and stitching overlapping regions of neighboring ones of all the dendrite structure feature maps marked with the dendrite centers obtained in step (3) by using an image registration algorithm that is based on mutual information, to obtain a dendrite structure feature map containing the marked dendrite centers in a full view field; and (5) Quantitative Distribution Characterization of the Number and Spacing of Dendrite Structures in a Full View Field within a Wide Range performing statistical distribution analysis on the number and spacing of dendrites in the dendrite structure feature map in a full view field obtained in step (4), to obtain quantitative statistical distribution data such as the position of each dendrite, the number of the dendrites and the spacing between two neighboring dendrites in a full view field within a wide range.

In step (1), the metallographic chemical corrosion is carried out by using a solution which is an alcohol solution with 2.0%-5.0% copper sulfate (m/V) and 50%-70% hydrochloric acid (V/V), or an aqueous solution with 1.0%-30.0% hydrofluoric acid (V/V), 20%-40% nitric acid (V/V) and 30%-40% glacial acetic acid (V/V), for 0.3 min-2 min.

In step (1), the object detection sample library includes a training set and a test set, wherein the training set is used for training to obtain the object detection model, and the test set is used for testing a reliability degree of the model.

In step (1), the object detection network is selected from the group consisting of Faster R-CNN, R-CNN, Fast R-CNN, Mask R-CNN, and SPP network frameworks; the network framework includes a feature extraction network, a pre-selection box network, fully connected layers and an output layer; wherein, the feature extraction network includes convolutional layers, ReLu layers, and pooling layers; the pre-selection box network uses RPNs (region proposal networks); the fully connected layers are two layers; and the output layer contains two parts, wherein one part outputs values indicating the probabilities that each pre-selection box corresponds to respective classification objects, for the purpose of determining the types of features in the pre-selection boxes, and the other part outputs values which are an array of four natural numbers, for the purpose of adjusting the position and size of each pre-selection box, the four natural numbers respectively corresponding to coordinates of the top left corner of the adjusted pre-selection box as well as the length and width of the pre-selection box.

Step (1) further includes a step of preprocessing original images in the dendrite structure feature map data set, in which before training, the original images in the dendrite structure feature data set are flipped, translated, rotated, and cropped.

In step (1), 5%-15% of view fields are randomly selected from the metallographic structure feature map of the standard metal material sample, and are manually marked to obtain a plurality of images containing marker boxes; after the marking is completed, the labeled plurality of images are input into the object detection network to carry out iterative training for 10000 to 50000 times to obtain the object detection model.

In step (3), detection of each image to be detected only takes 0.2 second.

In step (4), the mutual information of the dendrite structure feature maps is obtained by using entropies and joint entropies of any two dendrite structure feature maps in different view fields to determine the positions and sizes of neighboring overlapping regions, thus achieving identification and stitching of overlapping regions of neighboring dendrite structure feature maps.

Step (4) further includes performing mathematical processing on edge gray levels of the stitched dendrite structure feature map to achieve uniformity and fusion of gray levels.

In step (5), the dendrite structure feature map in a full view field obtained in step (4) is binarized to obtain a binary image containing only dendrite center points; the dendrite center points on the binary image is counted directly by using a connected region method to obtain the number of dendrite center points in a full view field; and based on coordinates of each dendrite center point, the distance between the dendrite center point and any other dendrite center point is calculated, the nearest neighboring point to the point at any angle is found and a spacing between the two points is recorded as a dendrite spacing of the point at the angle, and finally, dendrite spacings of all the points at any angle are calculated.

an average dendrite spacing $\lambda$ is calculated by formula (1):

$$\lambda = (S/N)^{0.5} \tag{1}$$

where $\lambda$ is the average dendrite spacing, S is the area of the view field, and N is the number of dendrites in the view field.

The method is used to characterize dendrite structures of nickel-based single crystal superalloys.

Compared with the prior art, the present invention has the following beneficial effects:

1. A dendrite spacing at present is mainly an average spacing between dendrites measured in a single field of view. The determination of the number of dendrites and the measurement of the spacing are mainly carried out by a manual identification and statistical method, which requires a large workload and has low efficiency. The object detection method based on deep learning in the present invention achieves automatic and rapid detection of a large number of dendrites in the field of view, and automatic calculation of the number of dendrites and the spacing between neighboring dendrites in any direction, thus greatly improving the detection efficiency.

2. An existing metallographic image method is mainly used for image analysis of a single field of view, and the area of an observed field of view and the number of dendrites are limited. In the present invention, a feature map of dendrite structures in a full view field within a large region of a material is obtained through automatic acquisition, stitching and fusion in the full view field within a wide range. In the present invention, statistical analysis of the dendrite structures is performed on images in the full view field, thereby greatly reducing the phenomenon of incomplete statistics of multiple dendrite structures at the edges in the case of observation of a single field of view. Thus, the method of the present invention has the advantages of a large field of view in statistics, high efficiency, and comprehensive information, and statistical data is more accurate and reliable in this way.

3. A dendrite spacing at present is mainly to get statistical average dendrite spacing, or to measure a dendrite spacing manually in a certain direction for a small number of images. The average dendrite spacing cannot reflect local feature information in different locations and different regions of a material. The method based on deep learning in the present invention can quickly determine the positions of all dendrite centers while ensuring high accuracy, and can calculate a dendrite spacing in any direction. In this way, not only can the average dendrite spacing in different regions be obtained in the full view field, but also the dendrite spacing from each dendrite to a neighboring dendrite in any direction can be obtained accurately. The statistical data are more comprehensive and rich. The method is also universal. For other feature micro-structures, it can achieve quick identification, automatic statistics and measurement by full-field image acquisition, stitching and fusion and deep learning.

BRIEF DESCRIPTION OF THE DRAWINGS

FIG. 3b is a labeled image corresponding to FIG. 3a;

FIG. 4b is a dendrite structure feature map with dendrite centers already detected, corresponding to FIG. 4a;

DETAILED DESCRIPTION OF THE EMBODIMENTS

Figure 1:
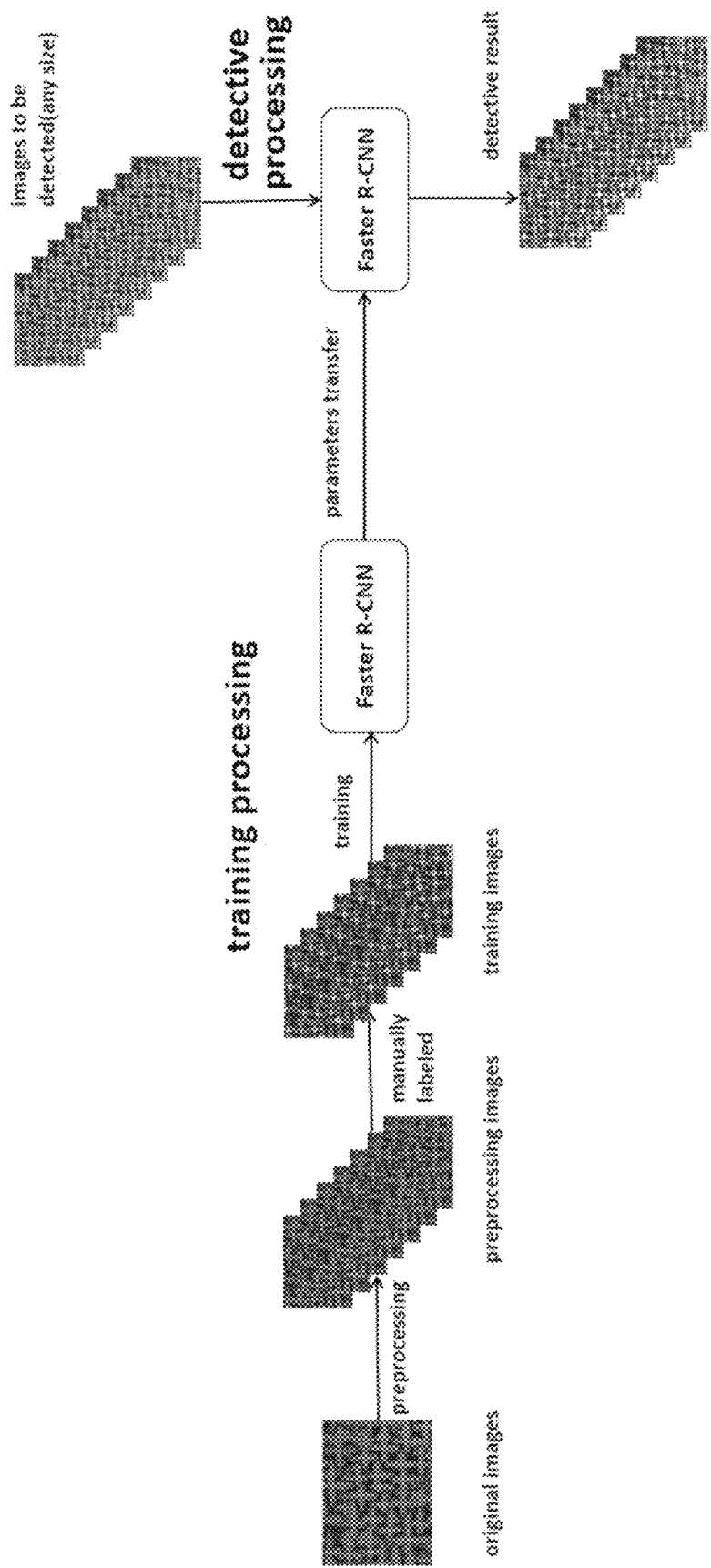
FIG. 1 is a schematic flow diagram of identifying dendrite structures in an embodiment of the present invention.

The present invention will be further described in conjunction with the accompanying drawings and embodiments.

The present invention provides a method for automatic quantitative statistical distribution characterization of dendrite structures in a full view field of metal materials, including the following steps:

(1) Establishment of an Object Detection Model Based on Deep Learning performing metallographic sample preparation on a standard metal material sample with the same material as a metal material to be detected, to obtain a smooth metallographic mirror surface; then performing metallographic chemical corrosion on the standard metal material sample so that the surface of the sample shows a clear and complete dendrite structure, and rinsing with water and absolute ethanol and blow-drying the same, wherein the metallographic chemical corrosion is carried out by using a solution which is an alcohol solution with 2.0%-5.0% copper sulfate (m/V) and 50%-70% hydrochloric acid (V/V), or an aqueous solution with 1.0%-30.0% hydrofluoric acid (V/V), 20%-40% nitric acid (V/V) and 30%-40% glacial acetic acid (V/V), for 0.3 min-2 min;

acquiring dendrite structure feature maps of the standard metal material sample after the metallographic chemical corrosion by using a fully automatic metallographic microscope, and establishing a dendrite structure feature map data set; labeling images in the dendrite structure feature map data set by using dendrite centers as objects to obtain images containing marker boxes, with the dendrite centers being inside the marker boxes, wherein labeled information includes a category and regional information of the object, the category indicating whether the marker box contains the dendrite center, and the regional information including the position of the dendrite center; and generating an object detection sample library from the labeled dendrite structure feature map data set; and establishing an object detection network, and training with the obtained object detection sample library to obtain an object detection model, wherein the training is carried out for 10000-50000 times;

the object detection sample library includes a training set and a test set, wherein the training set is used for training to obtain the object detection model, and the test set is used for testing a reliability degree of the model;

the object detection network is selected from the group consisting of Faster R-CNN, R-CNN, Fast R-CNN, Mask R-CNN, and SPP network frameworks; the network framework mainly includes a feature extraction network, a pre-selection network, fully connected layers and an output layer; wherein the feature extraction network includes convolutional layers, ReLu layers, and pooling layers; the pre-selection box network uses RPNs (region proposal networks); the fully connected layers are two layers; and the output layer contains two parts, wherein one part outputs values indicating the probabilities that each pre-selection box corresponds to respective classification objects, for the purpose of determining the types of features in the pre-selection boxes, and the other part outputs values which are an array of four natural numbers, for the purpose of adjusting the position and size of each pre-selection box, the four natural numbers respectively corresponding to coordinates of the top left corner of the adjusted pres-election box and the length and width of the pre-selection box;

preferably, to reduce the risk of overfitting during training due to insufficient training data, step (1) further includes a step of preprocessing original images in the dendrite structure feature map data set, in which before training, the original images in the dendrite structure feature data set are subjected to preprocessing operations such as flipping, translation, rotation, and cropping, to achieve the purpose of data enhancement;

(2) Automatic Acquisition of Dendrite Structure Feature Maps in a Full View Field of the Metal Material to be Detected performing metallographic sample preparation and metallographic chemical corrosion on the metal material to be detected, by using the same metallographic sample preparation and metallographic chemical corrosion process as in step (1), and then automatically acquiring a dendrite structure feature map in a full view field of the surface of the metal material to be detected after the metallographic chemical corrosion, by using a fully automatic metallographic microscope, wherein the number of the automatically acquired feature maps can reach 10000 or more;

(3) Automatic Identification and Rapid Positioning of Dendrite Structures inputting all images to be detected acquired in step (2) into the object detection model established in step (1), to directly obtain dendrite structure feature maps marked with the dendrite centers, wherein detection of each image to be detected in the process only takes 0.2 second;

(4) Automatic Stitching and Fusion of the Dendrite Structure Feature Maps in a Full View Field for all the dendrite structure feature maps marked with the dendrite centers obtained in step (3), using an image registration algorithm that is based on mutual information to obtain mutual information of the dendrite structure feature maps by using entropies and joint entropies of any two dendrite structure feature maps in different view fields to determine the positions and sizes of neighboring overlapping regions, thus achieving identification and stitching of overlapping regions of neighboring dendrite structure feature maps, and performing mathematical processing on edge gray levels of the stitched dendrite structure feature map to achieve uniformity and fusion of gray levels, thereby finally obtaining a dendrite structure feature map containing the marked dendrite centers in a full view field;

(5) Quantitative Distribution Characterization of the Number and Spacing of Dendrite Structures in a Full View Field within a Wide Range performing statistical distribution analysis on the number and spacing of dendrites in the dendrite structure feature map in a full view field obtained in step (4), to obtain quantitative statistical distribution data such as the position of each dendrite, the number of the dendrites and the spacing between two neighboring dendrites in a full view field within a wide range.

wherein the dendrite structure feature map in a full view field obtained in step (4) is binarized to obtain a binary image containing only dendrite center points; the dendrite center points on the binary image is counted directly by using a connected region method to obtain the number of dendrite center points in a full view field; and based on coordinates of each dendrite center point, the distance between the dendrite center point and any other dendrite center point is calculated, the nearest neighboring point to the point at any angle is found and a spacing between the two points is recorded as a dendrite spacing of the point at the angle, and finally, dendrite spacings of all the points at any angle are calculated, and an average dendrite spacing $\lambda$ is calculated by formula (1):

$$\lambda = (S/N)^{0.5} \quad (1)$$

where $\lambda$ is the average dendrite spacing, S is the area of the view field, and N is the number of dendrites in the view field.

Therefore, in the present invention, not only can the average spacing between dendrites in a view field of any size be quickly calculated through a formula in combination with image processing, but also the spacing distribution of dendrites in any direction can be quickly calculated.

The the present invention will be further described in conjunction with the accompanying drawings and embodiments.

Embodiment

The embodiment relates to a nickel-based single crystal superalloy for a turbine blade of an aero engine. The turbine blade is located at a position with the highest temperature, the most complicated stress, and the worst environment, and thus is regarded as the first key component of the engine. Directionally solidified single crystal superalloys have excellent high-temperature strength, fatigue resistance and fracture toughness, and good resistance to oxidation and hot corrosion, so they are preferred materials for turbine blades. A solidification structure in the process of directional solidification preparation of a single crystal superalloy is generally dendrite structure. The dendrite is caused by instability of a solid/liquid interface during the non-equilibrium solidification of the alloy and is controlled by a solidification process. A primary dendrite spacing is an important structure parameter of the single crystal superalloy. Reducing the primary dendrite spacing of the alloy can achieve optimization of an as-cast structure of the alloy, and can effectively reduce the eutectic and $\gamma'$ phase sizes of the as-cast alloy and optimize carbide morphology, thereby improving the fatigue life and durability of the superalloy. Therefore, quantitative characterization of a primary dendrite of a single crystal superalloy and statistical distribution of dendrite structure uniformity are important basis for evaluating the stability and reliability of a solidification process, and have important significance for improving the mechanical properties of a single crystal superalloy.

I. Establishment of an Object Detection Model Based on Deep Learning

A sample of a nickel-based single crystal superalloy standard bar matched with components prepared by a directional solidification process was subjected to coarse sanding, fine grinding, and fine polishing to produce a smooth metallographic mirror surface. Erosion is performed with an aqueous solution of 1.0%-30.0% hydrofluoric acid (V/V), 20%-40% nitric acid (V/V) and 30%-40% glacial acetic acid (V/V) for 0.3 min-2 min, so that the surface of the sample showed a clear and complete dendrite structure, and then the sample was rinsed with water and absolute ethanol and blow-dried. At a magnification of 50 times, a fully automatic microscope was used to perform sampling photography of metallographic structure maps of the sample surface after chemical corrosion, and the sampling position was random.

Figure 2:
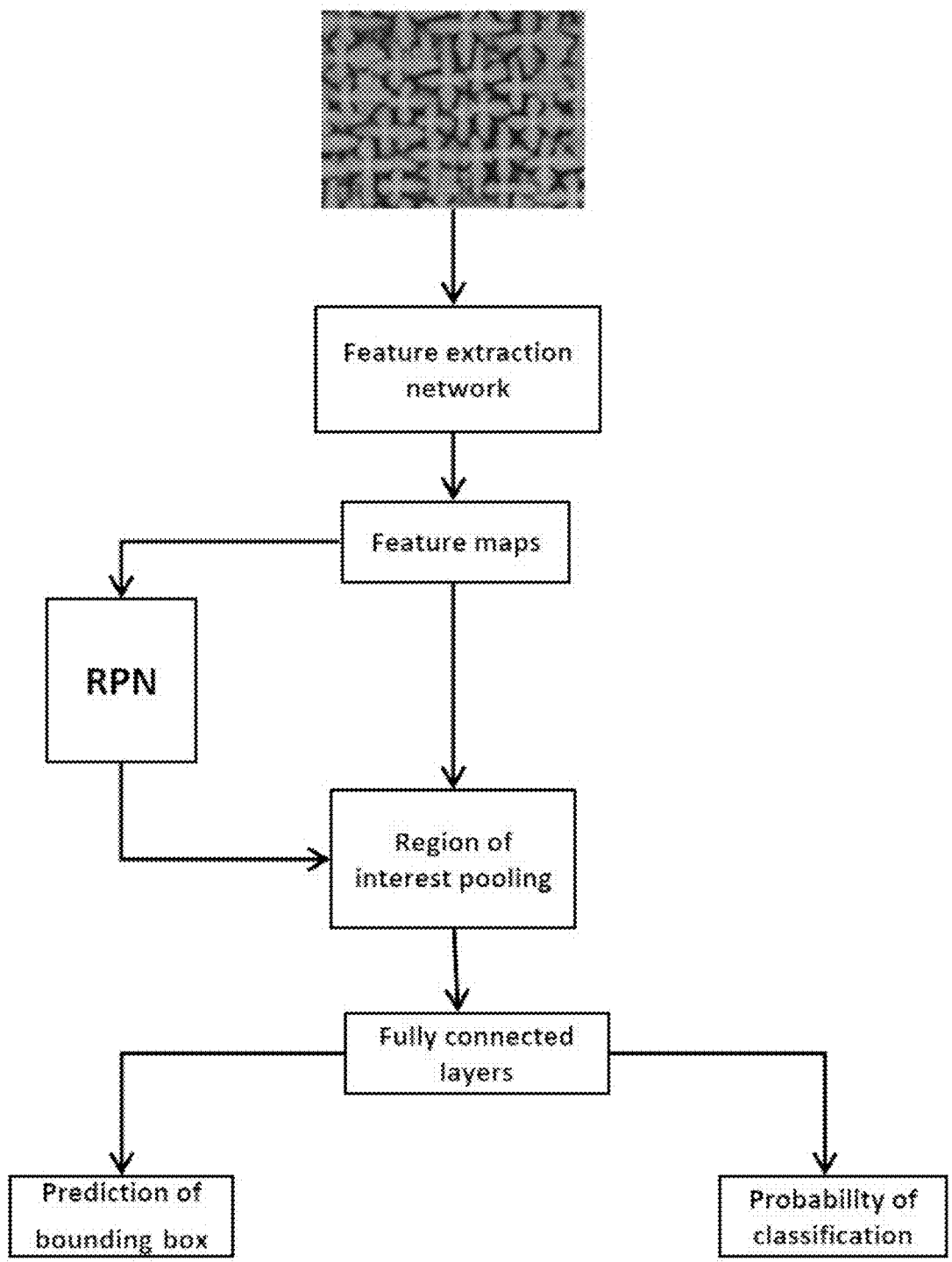
FIG. 2 shows an object detection network Faster R-CNN in an embodiment of the present invention.

FIG. 1 shows a flow diagram of establishing feature maps for identifying dendrite structures. To reduce the risk of overfitting in the training process due to insufficient training data, in this experiment, preprocessing operations such as flipping, translation, rotation and cropping were performed on the original images before training to achieve the purpose of data enhancement. Images in a dendrite structure feature map data set were labeled by using dendrite centers as objects to obtain images containing marker boxes, with the dendrite centers being inside the marker boxes, wherein marked information includes a category and regional information of the object, the category indicating whether the marker box contains the dendrite center, and the regional information including the position of the dendrite center; and an object detection sample library was generated from the marked dendrite structure feature map data set; and as shown in FIG. 2, an object detection network Faster R-CNN base on Deep Learning was established, and trained with the obtained object detection sample library to obtain an object detection model.

Figure 3A:
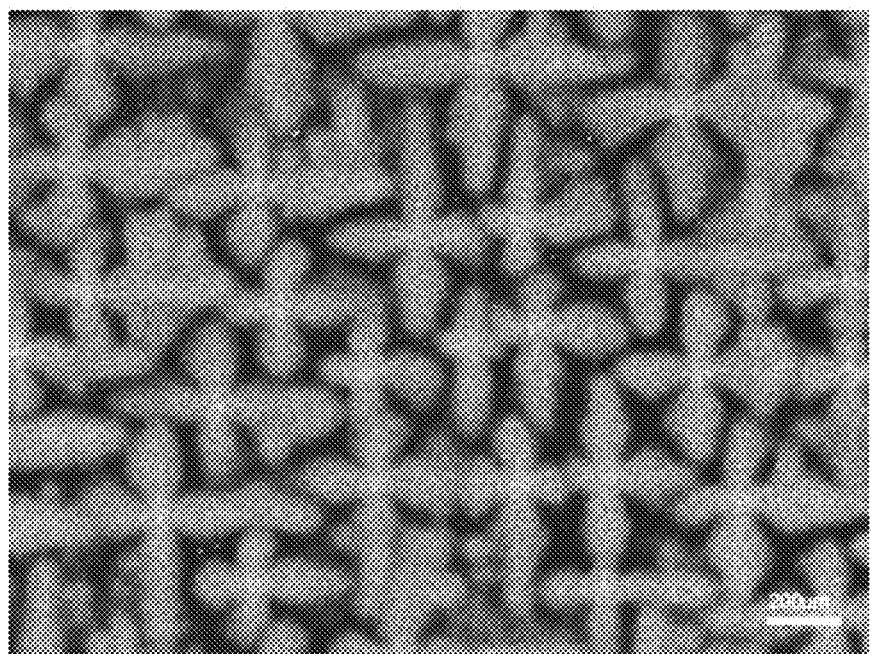
FIG. 3a is a randomly selected one of dendrite structure feature maps in an embodiment of the present invention.
Figure 3B:
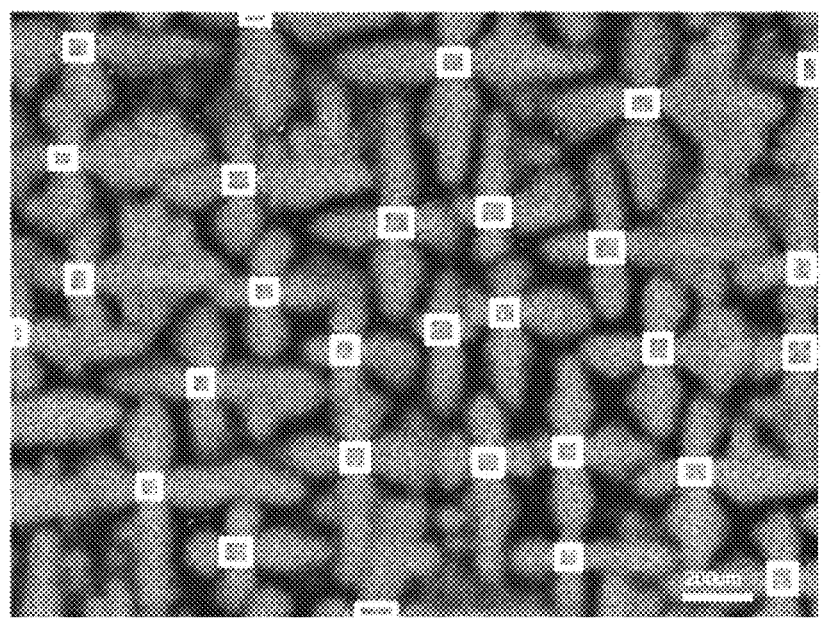

In the embodiment, 35 view fields (35 images) were randomly selected from the metallurgical structure feature map of the standard metal material sample, as shown in FIG. 3a, and were manually marked to obtain images containing marker boxes, as shown in FIG. 3b. After marking was completed, the marked images were input to the network shown in FIG. 2 for training to obtain an object detection model. In the embodiment, iterative trainings were performed for a total of 40000 times.

II. Automatic Acquisition of Dendrite Structure Feature Maps in a Full View Field Metallographic sample preparation and metallographic chemical corrosion were performed on the metal material to be detected, by using the same metallographic sample preparation and metallographic chemical corrosion process as in step I, and then a dendrite structure feature map was automatically acquired in a full view field of the surface of the metal material to be detected after the metallographic chemical corrosion, by using a fully automatic metallographic microscope at a magnification of 50 times, wherein for a circular cross section with a diameter of 15 mm, the number of automatically acquired view fields is 8×11, that is, the number of view fields in the direction X is 8, and the number of view fields in the direction Y is 11, and finally a feature map of primary dendrite structures in 88 view fields were obtained. In the embodiment, primary dendrite structures of totally four nickel-based single crystal superalloy samples from different processes were measured, and a total of 352 view fields are involved.

III. Automatic Identification and Rapid Positioning of Dendrite Structures

Figure 4A:
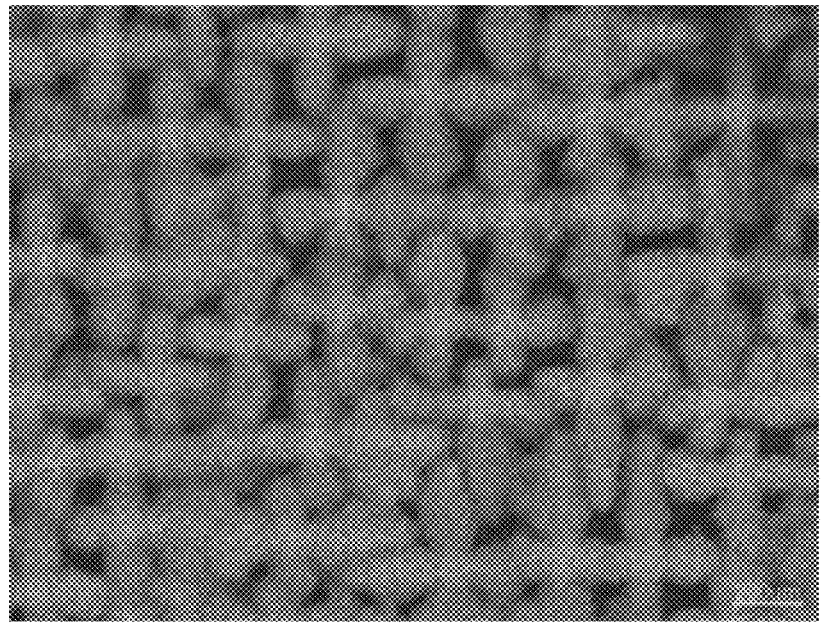
FIG. 4a is an image to be detected in an embodiment of the present invention.
Figure 4B:
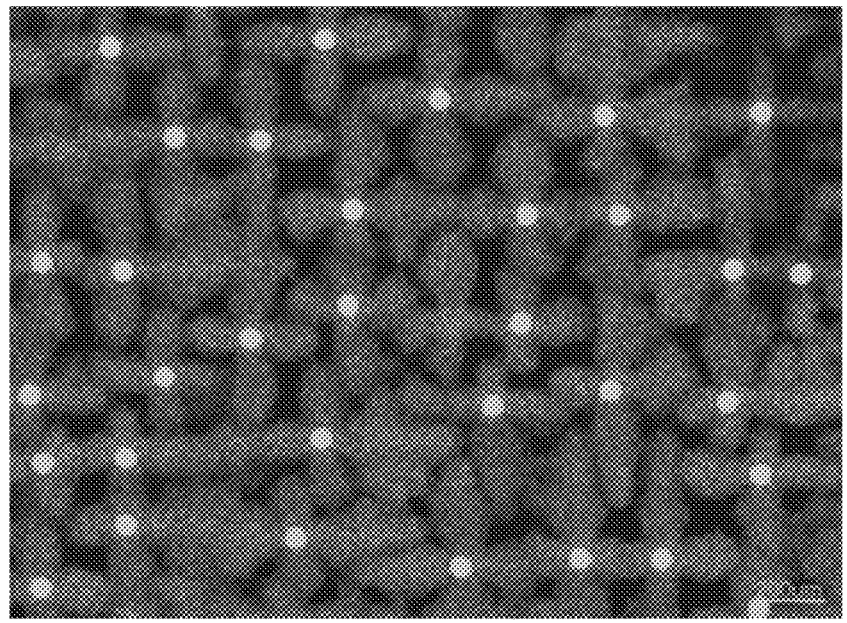
Figure 5A:
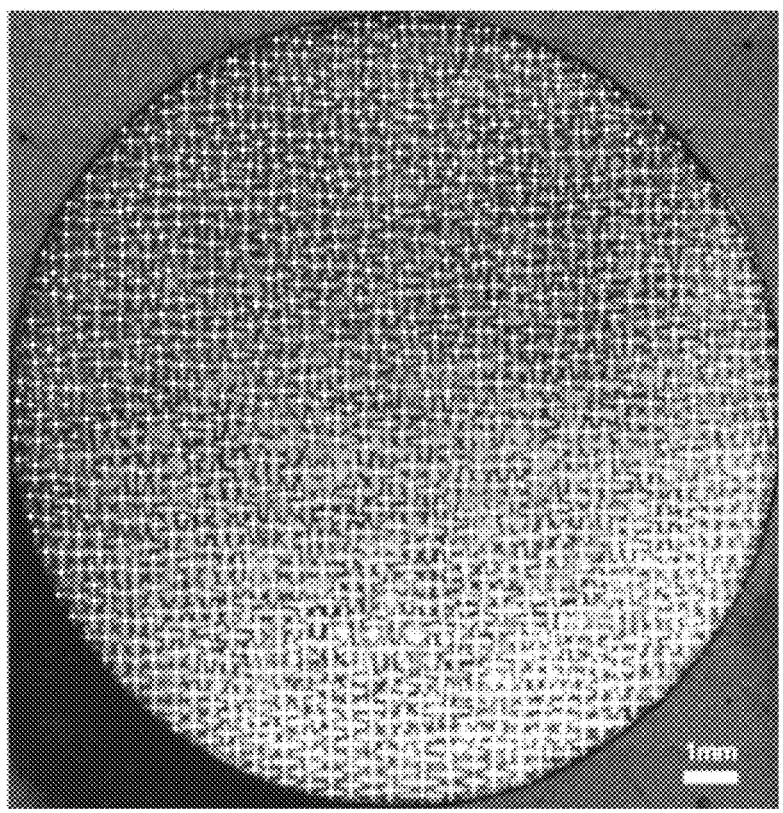
FIG. 5a is a dendrite structure feature map with marked dendrite centers in a full view field of a sample 1 in an embodiment of the present invention.
Figure 5B:
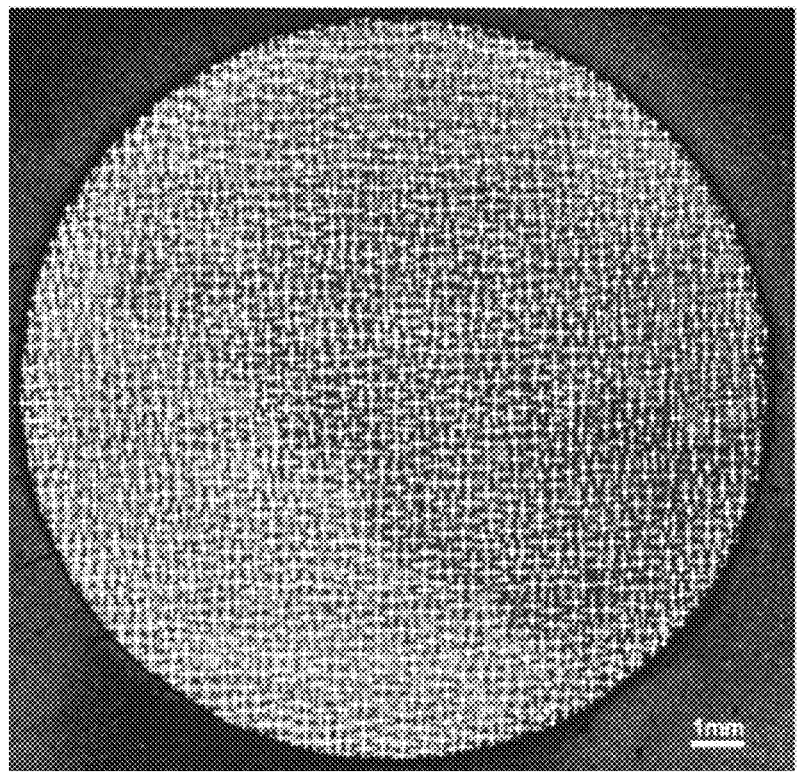
FIG. 5b is a dendrite structure feature map with marked dendrite centers in a full view field of a sample 2 in an embodiment of the present invention.
Figure 5C:
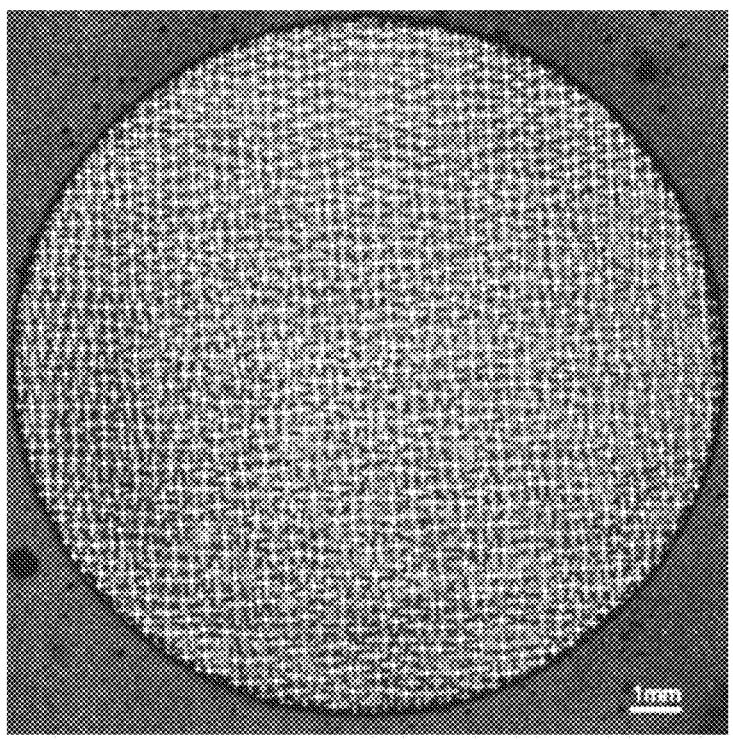
FIG. 5c is a dendrite structure feature map with labeled dendrite centers in a full view field of a sample 3 in an embodiment of the present invention.
Figure 5D:
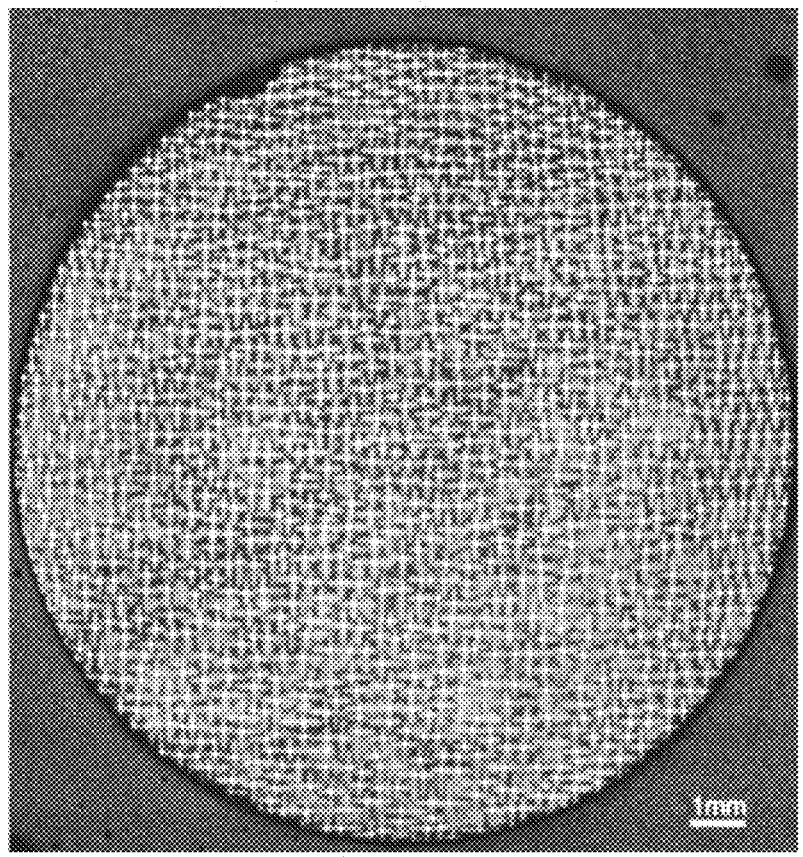
FIG. 5d is a dendrite structure feature map with labeled dendrite centers in a full view field of a sample 4 in an embodiment of the present invention.

All the images to be detected (as shown in FIG. 4a) were input to the established object detection model for detection to obtain dendrite structure feature maps marked with the dendrite centers as shown in FIG. 4b, wherein the detection speed is 0.2 second per image.

IV. Automatic Stitching and Fusion of the Dendrite Structure Feature Maps in a Full View Field For the feature maps automatically marked with the dendrite centers, an image registration algorithm based on mutual information MI was used to stitch the dendrite structure feature maps in different view fields into a complete full-field dendrite structure feature image, as shown in FIGS. 5a to 5d.

V. Quantitative Statistical Distribution Characterization of the Number and Spacing of Dendrite Structures within a Range of a Full View Field The dendrite structure feature map in a full view field is binarized to obtain a binary image containing only dendrite center points; and the center points on the binary images of the four nickel-based single crystal superalloy rod samples from different processes were directly counted by using a connected region method to obtain the numbers of dendrites in a full view field, which were then compared with the numbers of manually counted dendrites, to obtain results as shown in Table 1. This indicates that the method of the present invention is accurate and reliable.

Figure 6:
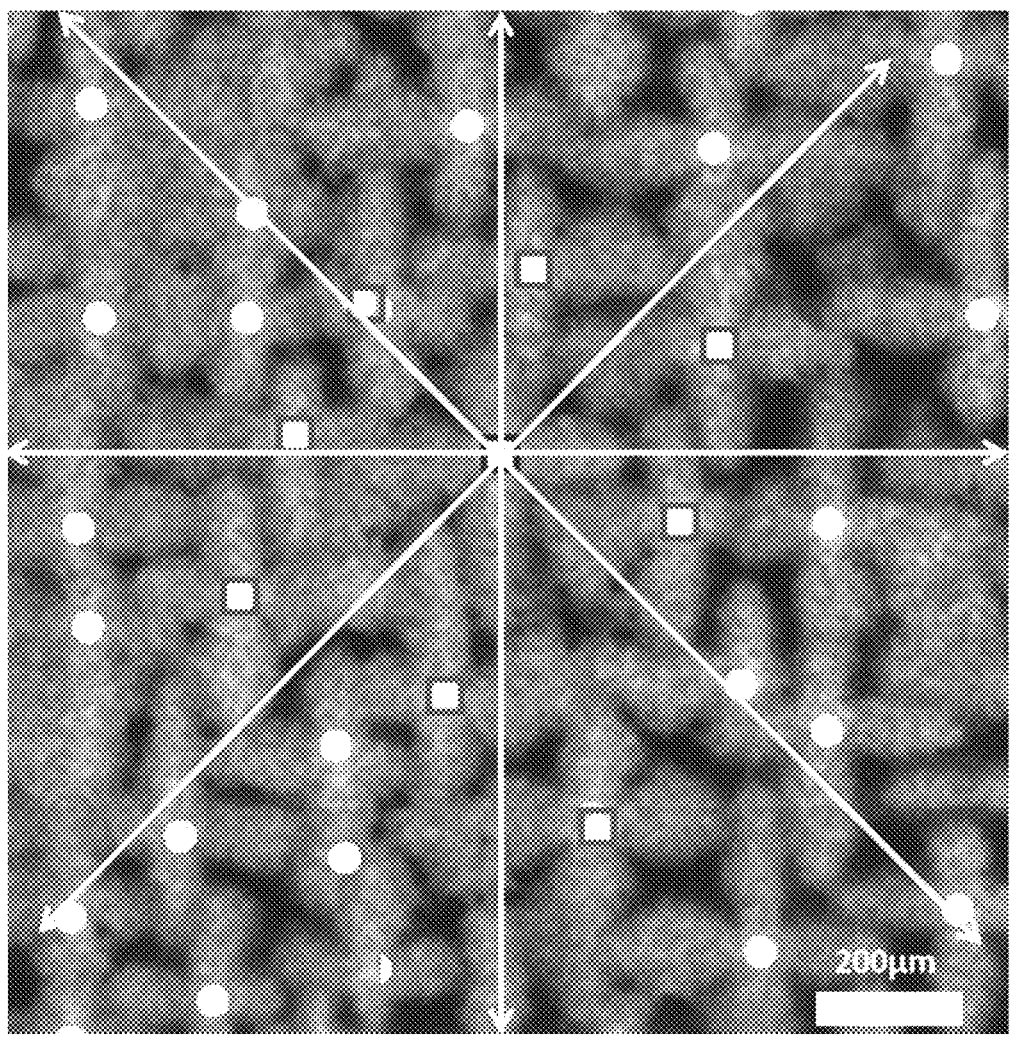
FIG. 6 is a schematic diagram of statistics in regions.
Figure 7:
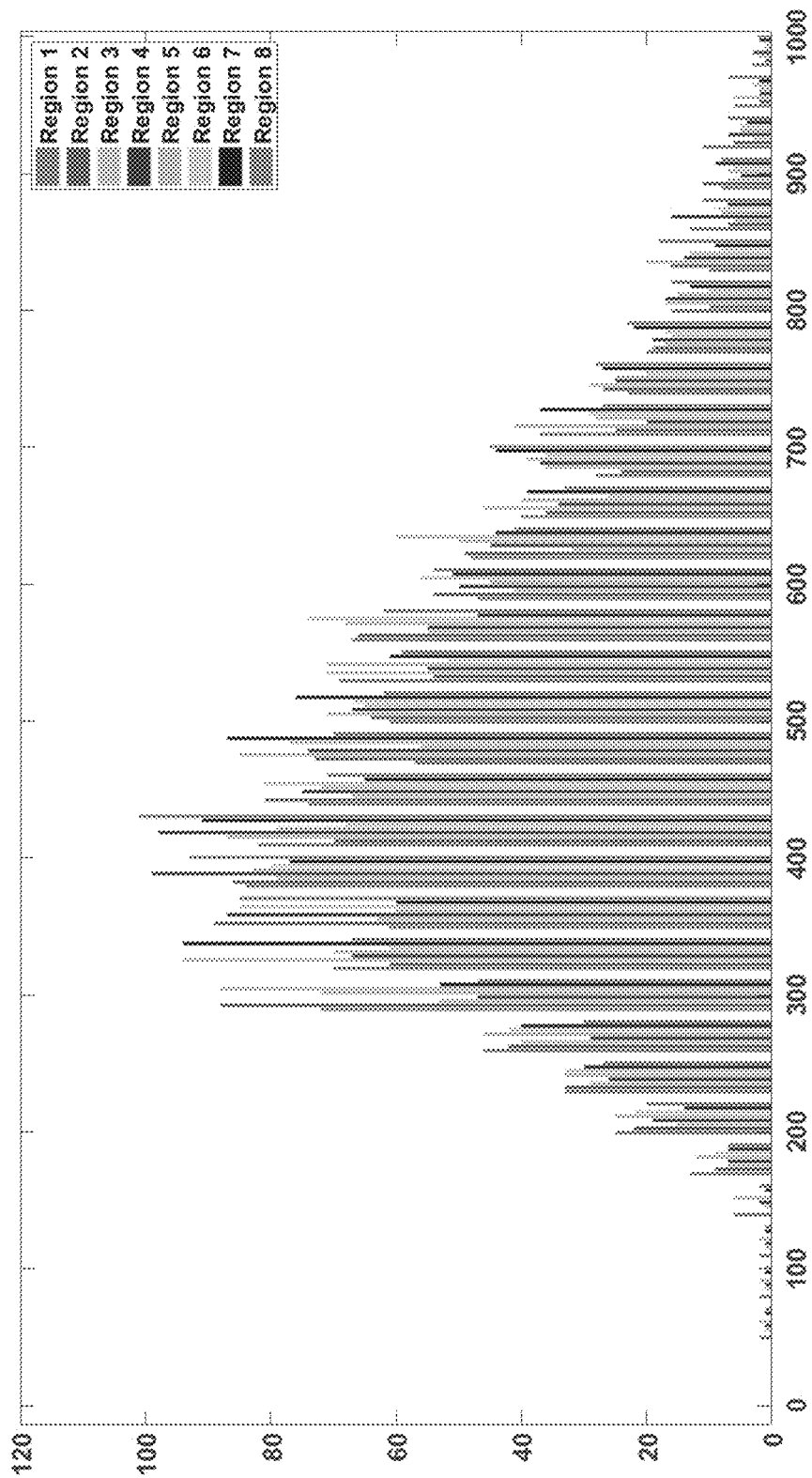
FIG. 7 is a histogram of all dendrite spacings in eight directions in a full view field of the sample 4 in an embodiment of the present invention.
Figure 8:
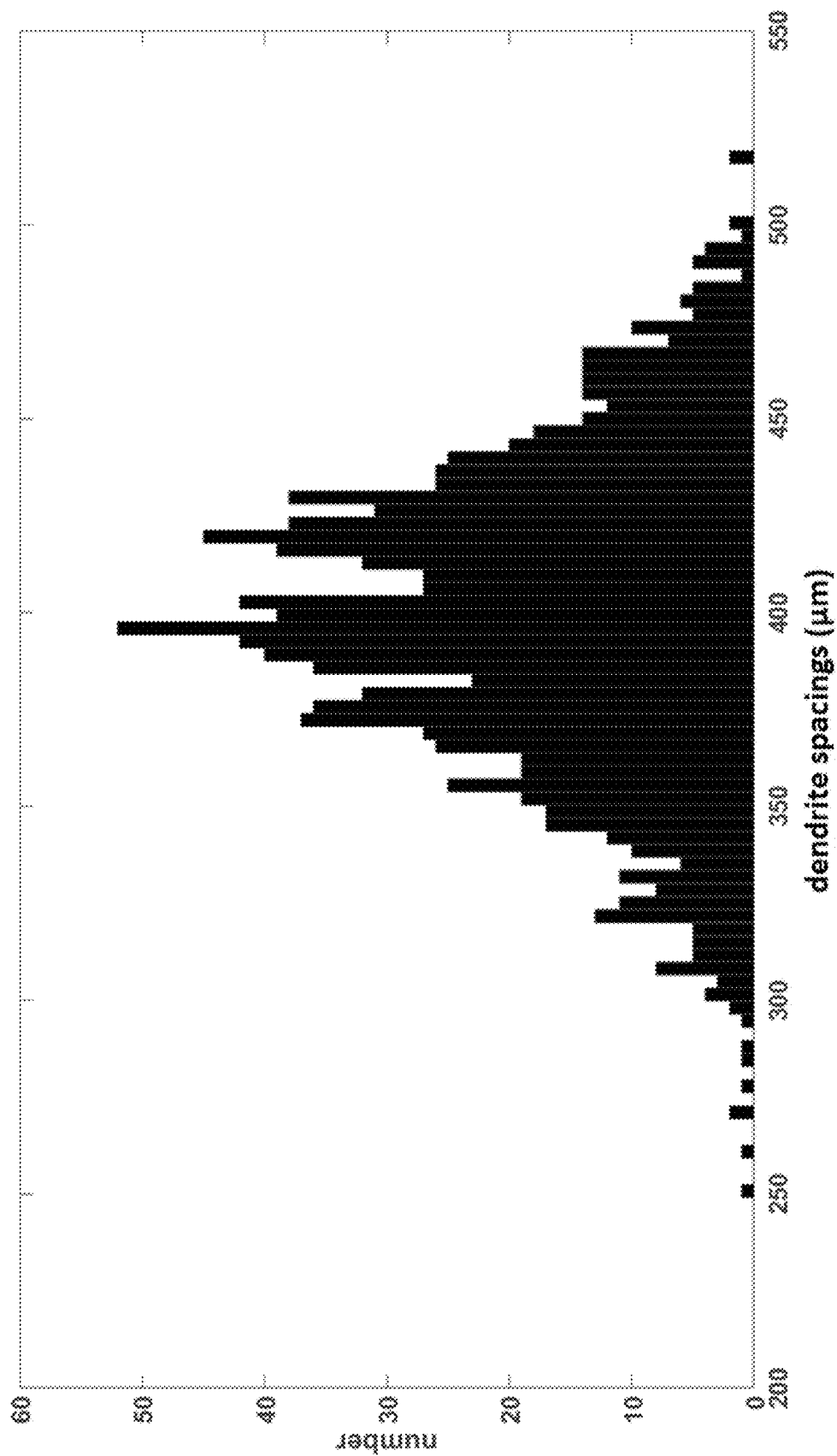
FIG. 8 is a histogram of average dendrite spacings of the sample 4 in an embodiment of the present invention.

According to the binary image containing only the dendrite center points, coordinates of any dendrite center point can be obtained, and the position of the closest dendrite to any dendrite in any direction was accurately found, and the distance therebetween was calculated. Using each dendrite center point as a coordinate origin, an entire screen is divided into eight regions, and all primary dendrite spacings in eight directions are obtained (as shown in FIG. 6). Using a sample 4 as an example, the histogram distribution of all the obtained dendrite spacings in the eight directions is shown in FIG. 7. For all dendrites, the dendrite spacings of each point in the 8 directions were averaged, to obtain a histogram as shown in FIG. 8.

As shown in Table 1, the numbers of dendrites in the sample 4 manually calculated and automatically identified were respectively 1195 and 1181, and the area of the sample 4 was 163.866 square millimeters. According to formula (1), average dendrite spacings obtained by statistical calculation through manual calculation and through automatic identification were respectively 370 μm and 372 μm. It can be seen readily from FIGS. 7 and 8 that peaks of the histograms are respectively at 395 μm and 385 μm, and most of the dendrite spacings are between 350 μm and 450 μm, which indicates that the quantitative statistical distribution analysis method provided in the present invention is in good correspondence with the traditional measurement method in terms of dendrite spacing characterization, but it can further indicate uneven distribution of the dendrite structures, and the dendrite spacings of the sample fluctuates within a range.

TABLE 1

Comparison of the number of primary dendrites automatically calculated and the number of dendrites directly measured

| Sample No. | 1 | 2 | 3 | 4 |
|---|---|---|---|---|
| Automatic statistical result | 1206 | 1280 | 1228 | 1181 |
| Manual measurement result | 1209 | 1408 | 1253 | 1195 |

The invention claimed is:

1. A method for automatic quantitative statistical distribution characterization of dendrite structures in a full view field of metal materials, comprising the following steps:
(1) establishment of an object detection model based on deep learning
performing metallographic sample preparation, polishing and chemical corrosion on a standard metal material sample with the same material as a metal material to be detected, so that the surface of the sample shows a clear and complete dendrite structure;
acquiring dendrite structure feature maps of the standard metal material sample after the metallographic chemical corrosion by using a fully automatic metallographic microscope, and establishing a dendrite structure feature map data set; labeling images in the dendrite structure feature map data set by using dendrite centers as objects to obtain images containing marker boxes, with the dendrite centers being inside the marker boxes, wherein marked information comprises a category and regional information of the object, the category indicating whether the marker boxes contains the dendrite center, and the regional information comprising the position of the dendrite center; and generating an object detection sample library from the marked dendrite structure feature map data set; and establishing an object detection network, and training with the obtained object detection sample library to obtain an object detection model;

(2) automatic acquisition of dendrite structure feature maps in a full view field of the metal material to be detected performing metallographic sample preparation and metallographic chemical corrosion on the metal material to be detected, by using the same metallographic sample preparation and metallographic chemical corrosion process as in step (1), and then automatically acquiring dendrite structure feature maps in a full view field of the surface of the metal material to be detected after the metallographic chemical corrosion, by using a fully automatic metallographic microscope;

(3) automatic identification and rapid positioning of dendrite structures inputting all images to be detected acquired in step (2) into the object detection model established in step (1), to directly obtain dendrite structure feature maps labeled with the dendrite centers;

(4) automatic stitching and fusion of the dendrite structure feature maps in a full view field identifying and stitching overlapping regions of neighboring ones of all the dendrite structure feature maps labeled with the dendrite centers obtained in step (3) by using an image registration algorithm that is based on mutual information, to obtain a dendrite structure feature map containing the marked dendrite centers in a full view field; and (5) Quantitative Distribution of the Number and Spacing of Dendrite Structures in a Full View Field within a Wide Range performing statistical distribution analysis on the number and spacing of dendrites in the dendrite structure feature map in a full view field obtained in step (4), to obtain quantitative statistical distribution data such as the position of each dendrite, the number of the dendrites and the spacing between two neighboring dendrites in a full view field within a wide range.

2. The method for automatic quantitative statistical distribution characterization of dendrite structures in a full view field of metal materials according to claim 1, wherein in step (1), the metallographic chemical corrosion is carried out by using a solution which is an alcohol solution with 2.0%-5.0% copper sulfate (m/V) and 50%-70% hydrochloric acid (V/V), or an aqueous solution with 1.0%-30.0% hydrofluoric acid (V/V), 20%-40% nitric acid (V/V) and 30%-40% glacial acetic acid (V/V), for 0.3 min-2 min.

3. The method for automatic quantitative statistical distribution characterization of dendrite structures in a full view field of metal materials according to claim 1, wherein in step (1), the object detection sample library comprises a training set and a test set, wherein the training set is used for training to obtain the object detection model, and the test set is used for testing a reliability degree of the model.

4. The method for automatic quantitative statistical distribution characterization of dendrite structures in a full view field of metal materials according to claim 1, wherein in step (1), the object detection network is selected from the group consisting of Faster R-CNN, R-CNN, Fast R-CNN, mask R-CNN, and SPP network frameworks; the network framework comprises a feature extraction network, a pre-selection box network, fully connected layers and an output layer; wherein the feature extraction network comprises convolutional layers, ReLu layers, and pooling layers; the pre-selection box network uses RPNs (region proposal networks); the fully connected layers are two layers; and the output layer contains two parts, wherein one part outputs values indicating the probabilities that each pre-selection box corresponds to respective classification objects, for the purpose of determining the types of features in the pre-selection boxes, and the other part outputs values which are an array of four natural numbers, for the purpose of adjusting the position and size of each pre-selection box, the four natural numbers respectively corresponding to coordinates of the top left corner of the adjusted pres-election box and the length and width of the pre-selection box.

5. The method for automatic quantitative statistical distribution characterization of dendrite structures in a full view field of metal materials according to claim 1, wherein step (1) further comprises a step of preprocessing original images in the dendrite structure feature map data set, in which before training, the original images in the dendrite structure feature data set are flipped, translated, rotated, and cropped.

6. The method for automatic quantitative statistical distribution characterization of dendrite structures in a full view field of metal materials according to claim 1, wherein in step (1), 5%-15% of view fields are randomly selected from the metallographic structure feature map of the standard metal material sample, and are manually labeled to obtain a plurality of images containing marker boxes; after the labeling is completed, the labeled plurality of images are input into the object detection network to carry out iterative training for 10000 to 50000 times to obtain the object detection model.

7. The method for automatic quantitative statistical distribution characterization of dendrite structures in a full view field of metal materials according to claim 1, wherein in step (3), detection of each image to be detected takes only 0.2 second.

8. The method for automatic quantitative statistical distribution characterization of dendrite structures in a full view field of metal materials according to claim 1, wherein in step (4), the mutual information of the dendrite structure feature maps is obtained by using entropies and joint entropies of any two dendrite structure feature maps in different view fields to determine the positions and sizes of neighboring overlapping regions, thus achieving identification and stitching of overlapping regions of neighboring dendrite structure feature maps.

9. The method for automatic quantitative statistical distribution characterization of dendrite structures in a full view field of metal materials according to claim 1, wherein step (4) further comprises performing mathematical processing on edge gray levels of the stitched dendrite structure feature map to achieve uniformity and fusion of gray levels.

10. The method for automatic quantitative statistical distribution characterization of dendrite structures in a full view field of metal materials according to claim 1, wherein in step (5), the dendrite structure feature map in a full view field obtained in step (4) is binarized to obtain a binary image containing only dendrite center points; the dendrite center points on the binary image is counted directly by using a connected region method to obtain the number of dendrite center points in a full view field; and based on coordinates of each dendrite center point, the distance between the dendrite center point and any other dendrite center point is calculated, the nearest neighboring point to the point at any angle is found and a spacing between the two points is recorded as a dendrite spacing of the point at the angle, and finally, dendrite spacings of all the points at any angle are calculated.

11. The method for automatic quantitative statistical distribution characterization of dendrite structures in a full view field of metal materials according to claim 10, wherein an average dendrite spacing $\lambda$ is calculated by formula (1):

$$\lambda = (S/N)^{0.5} \tag{1}$$

where $\lambda$ is the average dendrite spacing, S is the area of the view field, and N is the number of dendrites in the view field.

12. The method for automatic quantitative statistical distribution characterization of dendrite structures in a full view field of metal materials according to claim 1, wherein the method is used to characterize dendrite structures of nickel-based single crystal superalloys.

* * * * *